United States Patent [19]
Runge

[11] Patent Number: 5,827,220
[45] Date of Patent: Oct. 27, 1998

[54] CANNULA SYSTEM FOR A BIVENTRICULAR CARDIC SUPPORT SYSTEM OR A CARDIOPULMONARY BYPASS SYSTEM AND METHOD

[76] Inventor: Thomas M. Runge, P.O. Box 50045, Austin, Tex. 78763

[21] Appl. No.: 892,911

[22] Filed: Jul. 15, 1997

Related U.S. Application Data

[62] Division of Ser. No. 641,756, May 2, 1996, Pat. No. 5,688, 245.

[51] Int. Cl.$^6$ .................................................. A61M 31/00
[52] U.S. Cl. ................................................. 604/49; 604/8
[58] Field of Search ................................ 606/14, 2, 194, 606/192; 604/49, 53, 8, 28, 20, 96, 110

[56] References Cited

U.S. PATENT DOCUMENTS

| Re. 35,352 | 10/1996 | Peters ............................................. 604/4 |
| 5,702,368 | 12/1997 | Steens et al. ........................... 604/171 |

*Primary Examiner*—Corrine M. McDermott
*Assistant Examiner*—Cris L. Rodriguez
*Attorney, Agent, or Firm*—Brady, O'Boyle & Gates

[57] ABSTRACT

A cannula system for a biventricular cardiac support system or a cardiopulmonary bypass system wherein a first cannula having a pair of side-by-side lumens is adapted to be positioned within the left atrium and left ventricle and aorta of a patient. Blood from the left atrium and left ventricle drains into one of the lumens in the first cannula and is conveyed to the inlet of a pulsatile flow cardiopulmonary bypass pump from where it is pumped through the other lumen into the aorta of the patient. An inflatable balloon is provided at the distal end of the first cannula for holding the distal end of the cannula in the aorta above the aortic valve, The first cannula includes an axially extending bore communicating with a space in the aorta between the inflated balloon and the aortic valve for conveying cardioplegic solution to the space communicating with the left and right arteries of the patient. A second cannula having a pair of side-by-side lumens is adapted to be positioned within the right atrium and right ventricle and pulmonary artery of the patient. Blood from the right atrium and right ventricle flows into one of the lumens in the second cannula and is conveyed to the pulsatile flow cardiopulmonary bypass pump from where it is pumped through the other lumen into the pulmonary artery of the patient.

2 Claims, 3 Drawing Sheets

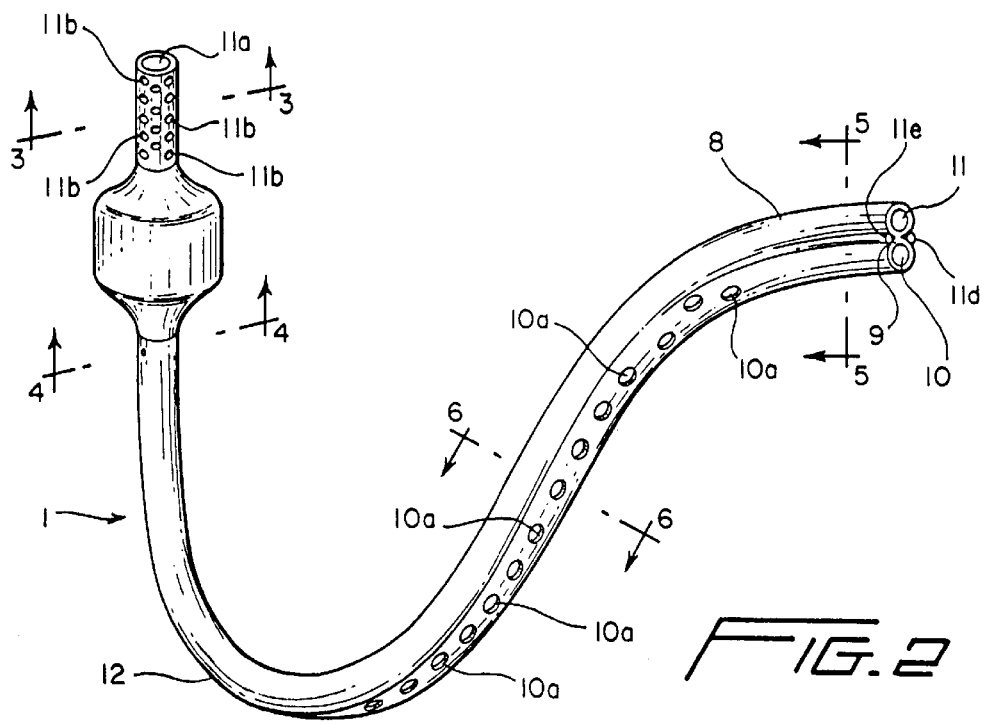
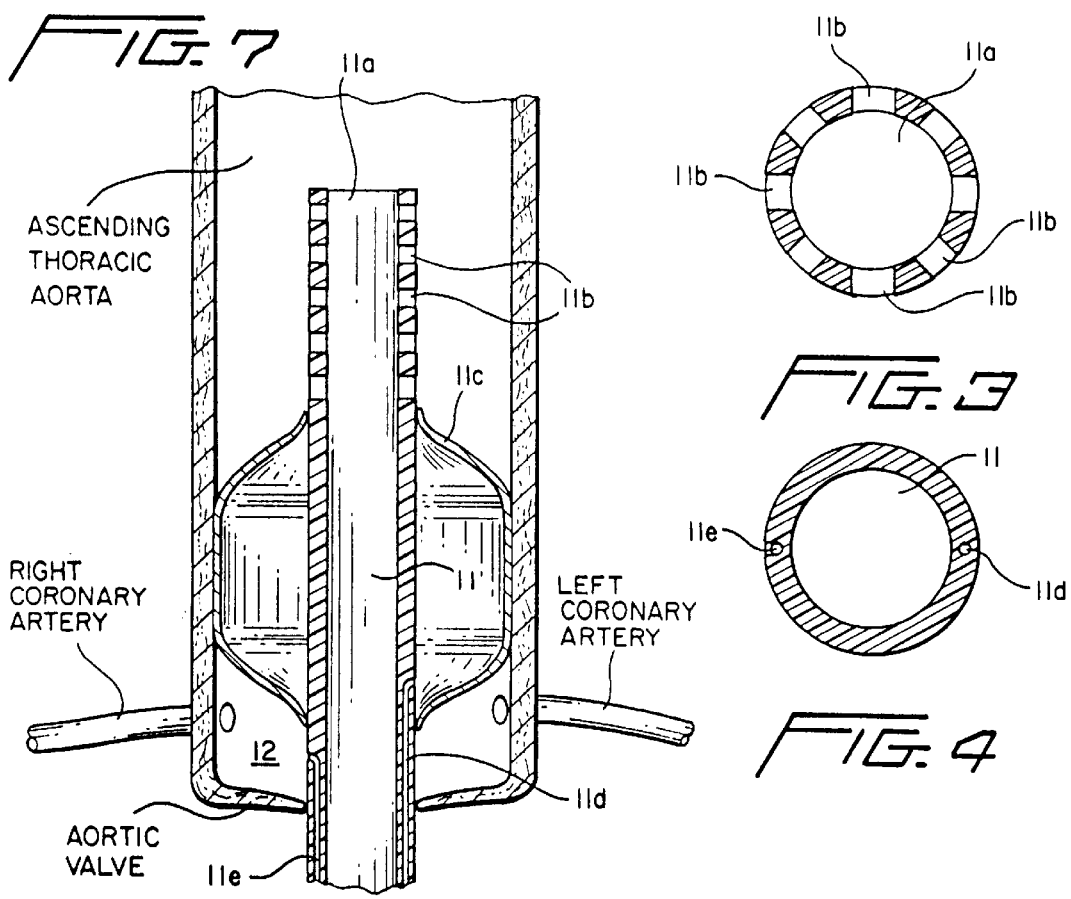

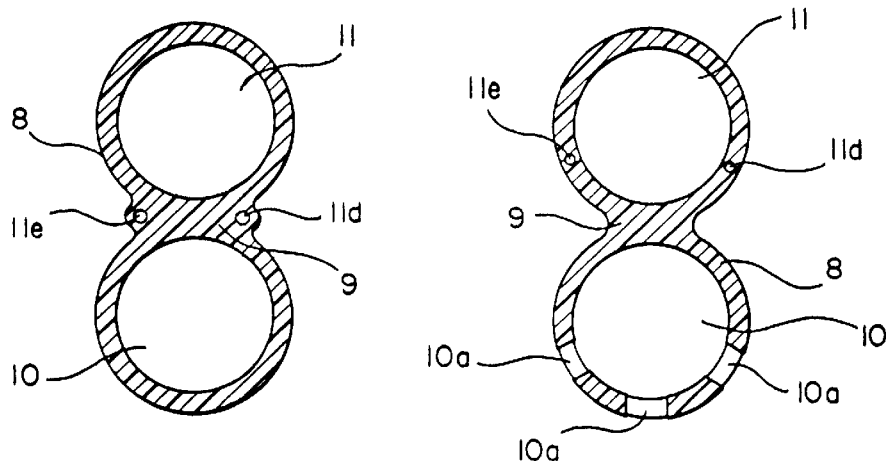
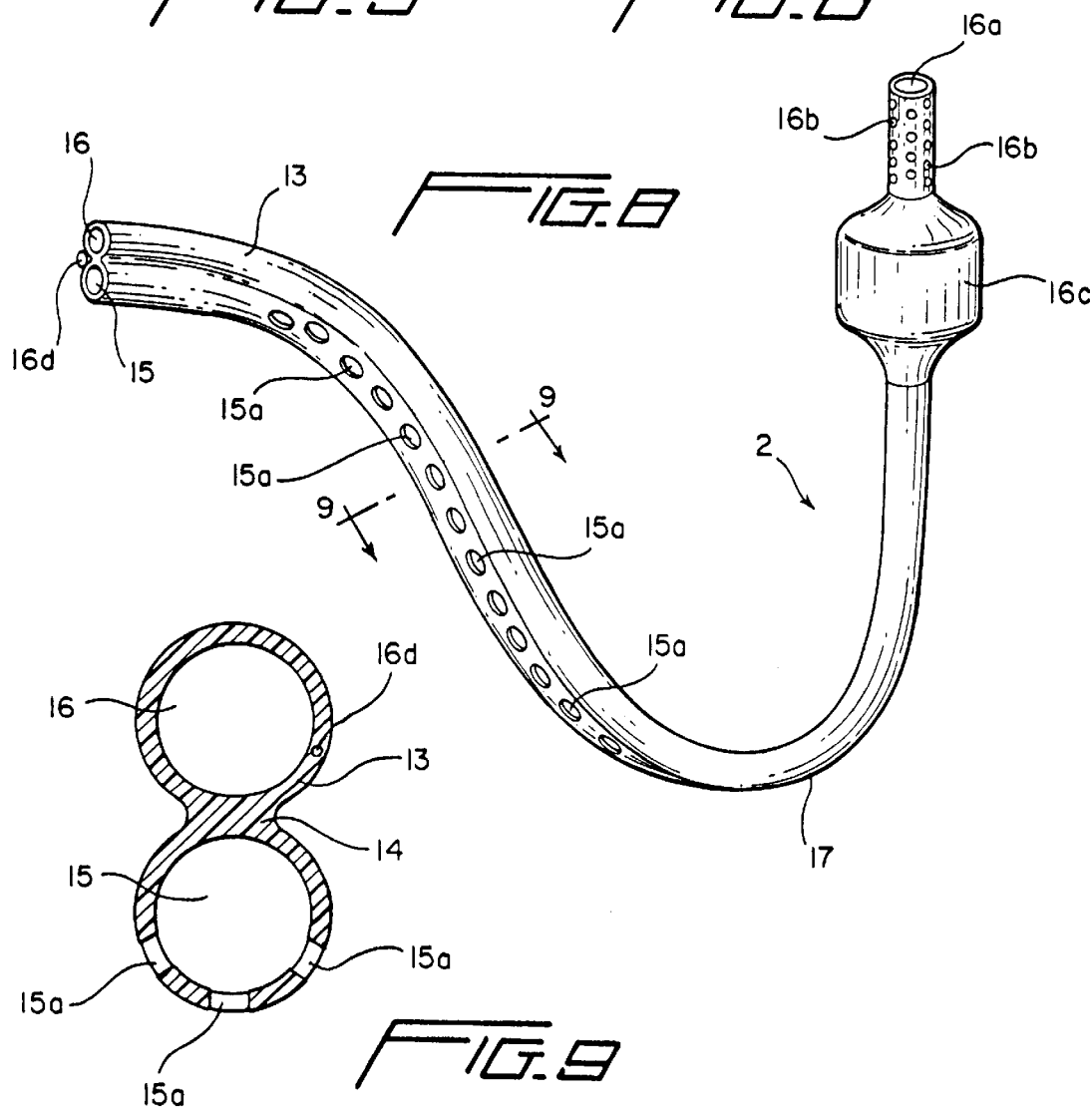

nat# CANNULA SYSTEM FOR A BIVENTRICULAR CARDIC SUPPORT SYSTEM OR A CARDIOPULMONARY BYPASS SYSTEM AND METHOD This application is a division of application Ser. No. 08/641,756, filed May 2, 1996, now U.S. Pat. No. 5,688,245.

BACKGROUND OF THE INVENTION

In Applicant's co-pending application, Ser. No. 8/376, 964, filed Jan 12, 1995, there is disclosed a biventricular pulsatile cardiac support system having a mechanically balanced stroke volume wherein a pair of side-by-side valveless, compressible conduits extend through the compression chamber of a pulsatile flow cardiopulmonary bypass pump and a passive exterior valve positioned at the inlet and the outlet of the pump. The inlets of the conduits communicate with the right and left atria of the patient's heart and the outlets of the conduits communicate with the pulmonary artery and aorta so that the volume of blood passing from the right atrium through the right ventricle, to the pulmonary artery, is substantially balanced with the volume of blood passing from the left atrium through the left ventricle to the aorta, In his continued research and experimentation in the field of cardiac support systems, Applicant has invented a new and improved cannula to be substituted for the pairs of conduits inserted into the patient's heart as disclosed in the above-mentioned pending application.

SUMMARY OF THE INVENTION

The cannula of the present invention comprises, essentially, a plastic tube having a transverse, axially extending wall or partition at an end portion of the tube to thereby provide a pair of side-by-side first and second lumens. The distal end of the transverse wall merges with the side wall of the tube, to thereby terminate and close the distal end of the first lumen; a plurality of orifices are provided in the side wall of the tube communicating with the first lumen. The distal end of the second lumen has a large end orifice and a plurality of smaller orifices in the side wall of the tube. An inflatable balloon is provided at the distal end of the second lumen positioned below and adjacent to the side wall orifices for selectively seating the second lumen in the ascending thoracic aorta or the pulmonary artery of the patient. First and second cannulas are adapted to be inserted into a patient's heart so that the side wall orifices in the first lumen of the first cannula communicates with the left atrium and left ventricle of the patient and the distal end of the second lumen in the first cannula is inserted into the ascending thoracic aorta of the patient, the balloon being inflated for seating the cannula in the aorta. The side wall orifices in the first lumen of the second cannula communicates with the right atrium and right ventricle of the patient and the distal end of the second lumen of the second cannula extends into the pulmonary artery of the patient, the balloon being inflated for seating the second cannula in the pulmonary artery of the patient. The first cannula inserted into the ascending thoracic aorta includes an axially extending bore in the wall of the second lumen communicating with a chamber provided between the lower end of the inflated balloon and the aortic valve for supplying oxygenated blood and cardioplegic solution to the coronary arteries communicating with the heart muscle myocardium.

The proximate end of each lumen in each cannula communicates with a respective tube extending through the compression chamber of a pre-load responsive pulsatile flow pump.

By this construction and arrangement, oxygenated blood is drained from the left atrium and left ventricle into the first lumen of the first cannula and through a first tube to the inlet side of the pump; the second lumen of the first cannula is connected to a second tube extending from the outlet of the pump for supplying oxygenated blood to the aorta, and the blood from the right atrium and right ventricle flows into the first lumen of the second cannula and through a third tube extending through the inlet of the pump; the second lumen of the second cannula is connected to a fourth tube extending from the outlet of the pump for supplying blood to the pulmonary artery, whereby both the right and left lungs, as well as the systemic circulation via the aorta receive vigorous pulsatile flow from the pre-load responsive pulsatile pump which automatically balances output from right and left ventricles on a beat-by-beat basis, to thereby prevent overloading either the right or left side of the circulatory system.

The system of the present invention accomplishes total cardiopulmonary bypass using the patient's own lungs for oxygenation, thus, eliminating the need for artificial oxygenators, and also the system can be employed for total or partial right and left ventricular support in critically ill patients, not of a surgical type. It also avoids cannula perforation of the aorta during cardiopulmonary bypass.

BRIEF DESCRIPTION OF THE DRAWINGS

FIG. 2 is a perspective view of the cannula of the present invention for use on the left side of the heart;

FIG. 3 is a view taken along line 3—3 of FIG. 2;

FIG. 4 is a view taken along line 4—4 of FIG. 2;

FIG. 5 is a view taken along line 5—5 of FIG. 2;

FIG. 6 is a view taken along line 6—6 of FIG. 2;

FIG. 7 is a fragmentary, sectional view illustrating the distal end of the cannula positioned within the aorta of a heart;

FIG. 8 is a perspective view of the cannula of the present invention for use on the right side of the heart; and FIG. 9 is a view taken along line 9—9 of FIG. 8.

DESCRIPTION OF THE PREFERRED EMBODIMENTS

Figure 1:
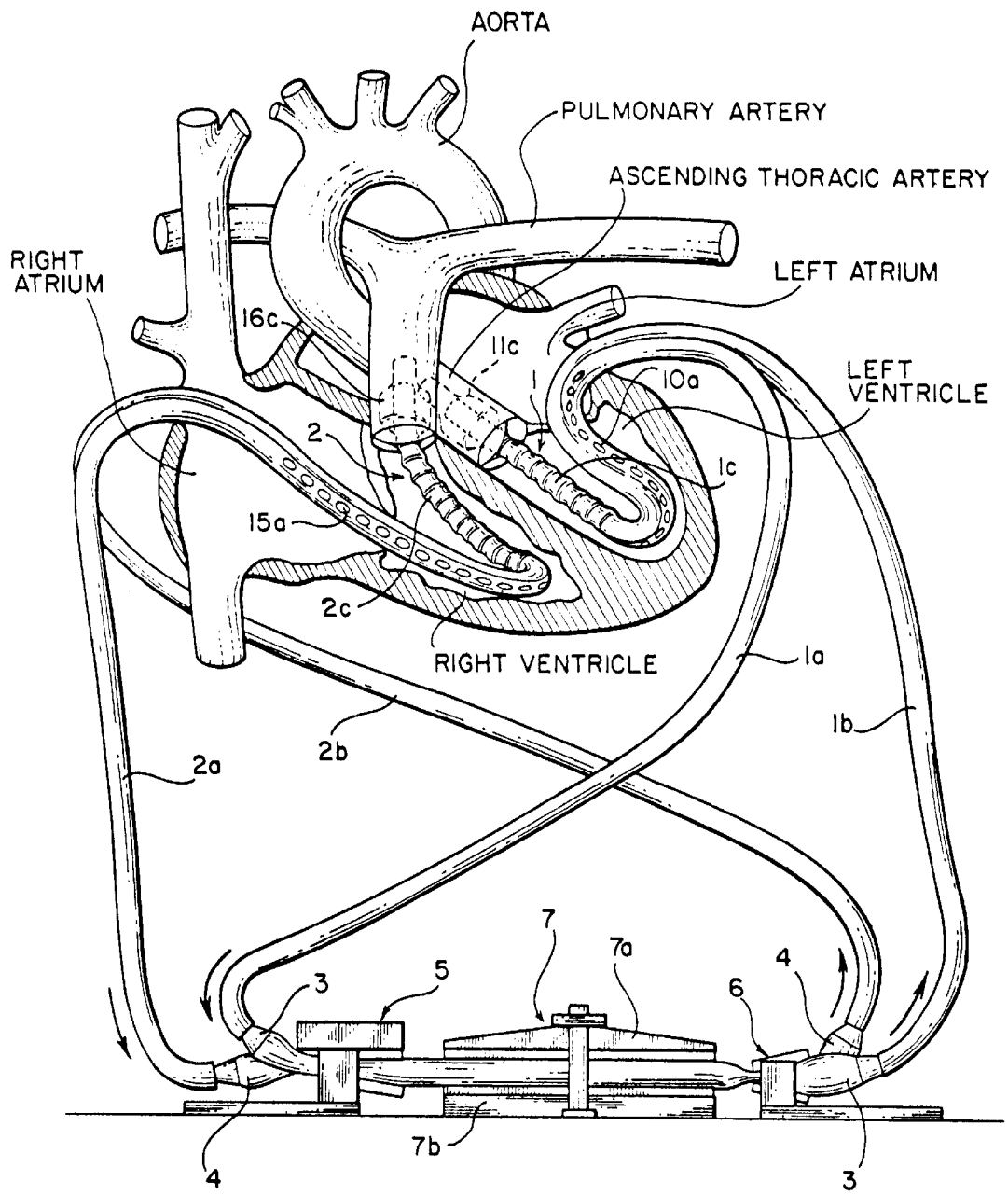
FIG. 1 is a diagrammatic view showing the use of the cannula of the present invention in a cardiac support system.

Referring to the drawings and, more particularly, to FIG. 1, the cannulas 1 and 2 of the present invention are adapted to respectively communicate with the left ventricle and ascending thoracic aorta, and the right ventricle and pulmonary artery of a patient's heart. The cannula 1 communicates with a tube 1a connected to the inlet of a compressible conduit 3, and a tube 1b connected to the outlet of the compressible conduit 3. Similarly, the cannula 2 communicates with a tube 2a connected to the inlet of a compressible conduit 4, and a tube 2b connected to the outlet of the compressible conduit 4. The compressible conduits 3 and 4 are of the type disclosed in Applicant's U.S. Pat. No. 5,437,601, dated Aug. 1, 1995, and extend through external inlet and outlet plate valves 5 and 6 of the type disclosed in U.S. Pat. No. 5,383,839, the disclosures of which patents are incorporated herein by reference. The portions of the compressible conduits 3 and 4 between the inlet and outlet valves 5 and 6 form sacks which extend through the compression chamber of a pulsatile flow cardiopulmonary bypass pump 7 of the type disclosed in U.S. Pat. No. 4,553,532, dated Nov. 19, 1985, which includes a moveable compression plate 7a and a fixed plate 7b.

The details of the construction of the aorta cannula 1 are illustrated in FIGS. 2 to 6 and comprise a plastic tube 8 having a transverse, axially extending wall or partition 9 to thereby form a pair of side-by-side lumens 10 and 11. The distal end of the transverse wall 9 merges with the side wall of the tube 8 as at 12, to thereby terminate and close the distal end of the lumen 10 at this point. A plurality of aspiration orifices 10a are provided in the side wall of the tube 8 communicating with the lumen 10.

The lumen 11 extends the full length of the tube 8 and terminates at its distal end with a large end orifice 11a and a plurality of smaller orifices 11b in the side wall of the tube 8 communicating with the lumen 11, An inflatable balloon 11c is provided at the distal end portion of the lumen 11 positioned below and adjacent to the side wall orifices 11b for seating the lumen 11 in the ascending thoracic aorta, as shown in FIG. 7. An axially extending bore 11d is provided in the side wall of the tube 8 communicating the interior of the balloon 11c with a source of an inflation medium (not shown) which can consist of air, physiologic saline, nitrous oxide, helium, and the like. Another axially extending bore 11e is provided in the side wall of the tube 8 communicating with a chamber 12 defined by the lower end wall of the balloon 11c and the aortic valve. The chamber 12 communicates with the left and right coronary arteries of the patient which supply the myocardium with oxygenated blood and cardioplegic solution. A cold cardioplegic solution, such as the patient's blood plus potassium, is introduced by the operative team into the chamber 12 through the bore 11e, making cannulation of the orifices of the coronary arteries unnecessary, to thereby both cool the myocardium to diminish oxygen demand, and to arrest the heart in diastole for the benefit of the surgeon during cardiac surgical procedures.

The construction of the cannula 2, as shown in FIGS. 8 and 9, is similar to that of cannula 1 and comprises a plastic tube 13 having a transverse, axially extending wall or partition 14 to thereby form a pair of side-by-side lumens 15 and 16. The distal end of the transverse wall 14 merges with the side wall of the tube 13, as at 17, to thereby terminate and close the distal end of the lumen 15 at this point. A plurality of aspiration orifices 15a are provided in the side wall of the tube 13 communicating with the lumen 15.

The lumen 16 extends the full length of the tube 13 and terminates at its distal end with a large end orifice 16a and a plurality of smaller orifices 16b in the side wall of the tube 13 communicating with the lumen 16. An inflatable balloon 16c is provided at the distal end portion of the lumen 16 positioned below and adjacent to the side wall orifices 16b. Inflation of the balloon 16c is accomplished by all axially extending bore 16d provided in the wall of the tube 13 communicating the balloon 16c with a source of inflation. Cannula 2 does not require a cardioplegic line; such as bore 11e in cannula 1.

Referring to FIG. 1, the cannula 1 is placed in the system by guiding the distal end of the cannula into the ascending thoracic aorta, inflating the balloon 11c to anchor the cannula in place and positioning the aspiration orifices 10a in the left atrium and left ventricle, The cannula 2 is similarly placed in the system by guiding the distal end thereof into the pulmonary artery, inflating the balloon 16c to anchor the cannula in place, and positioning the aspiration orifices 15a in the right atrium and left atrium.

The cannula 1 and 2 are guided into place by the surgeon employing a conventional guide mechanism used in fiber optic hardware under echocardiographic visualization wherein an echocardiographic transducer is placed on the patient's heart, and each cannula 1 and 2 is attached to a respective intraluminal guidable flexible cable. When in place, oxygenated blood in the left atrium and left ventricle will drain through the orifices 10a into the lumen 10 communicating with the tube 1a connected to the inlet of the compressible conduit 3, and the ventricles are thereby decompressed. The oxygenated blood is then pumped through the outlet of conduit 3 and into tube 1b communicating with the lumen 11 and out through the large end orifice 11a and side wall orifices 11b where a vigorous, pulsatile flow of oxygenated blood of physiologic morphology is produced in the aorta and then distributed to all parts of the body, except the coronary arteries which are fed the cold oxygenated cardioplegic solution through bore 11e, as noted above.

The cannula 2 is positioned so that the distal end of the cannula is placed in the pulmonary artery so that the balloon 16c is positioned above the pulmonic valve and then inflated to ensure closure of the exit to the right ventricle so that there will be no regurgitation of blood into the right ventricle. The aspiration orifices 15a are positioned in the right atrium and right ventricle so that blood will drain therefrom into the orifices 15a through the lumen 15 communicating with tube 2a connected to the inlet of compressible conduit 4. The blood is then pumped through the outlet of conduit 4 into tube 2b communicating with the lumen 16 to the pulmonary artery. Hence, both the right and left lungs, as well as the systemic circulation via the aorta, receive vigorous pulsatile flow from the pre-load responsive pulsatile pump 7 which automatically balances the output from the right and left ventricles on a beat-by-beat basis so that there is no problem of overloading either the right or left side of the circulatory system.

The cannulas 1 and 2 can be provided with corrugated portions 1c and 2c to not only facilitate the manipulation of this portion of the cannula, but also to vary the effective length of the cannulas to fit the patient's heart dimensions.

From the above description, it will be appreciated by those skilled in the art that the system of the present invention accomplishes total cardiac support using the patient's own lungs to oxygenate the blood, to thereby reduce the degree of hemodilution by eliminating the need for artificial oxygenation.

The vigorous pulsatile flow produced by the system of the present invention reduces the incidence and severity of memory deficit post myocardial revascularization surgery by successful delivery of physiologic pulsatile flow to the brain, and the reduction in the degree of hemodilution, thereby enhancing the oxygen carrying capacity of the blood.

The system of the present invention also precludes the customary perforation of the aorta by a cannula, thus preventing embolization of plaque material to the brain and also possible hemorrhage.

It is to be understood that the form of the invention herewith shown and described is to be taken as a preferred example of the same, and that various changes in the shape, size, and arrangement of parts may be resorted to, without departing from, the spirit of the invention or scope of the subjoined claims.

I claim:

1. A method of inserting a cannulation system into a patient's heart comprising the steps of:
   a. selectively accessing the heart via the right or left atrial appendage, or both;
   b. placing an echocardiographic transducer on the heart;

c. attaching at least one cannula to a respective intraluminal guidable flexible cable;
d. selectively positively directing and guiding the cannula and associated guide cable through the atrial and ventricles to the pulmonary artery or aorta;
e. continuously visualizing the direction of the cannula and associated guide; and
f. firmly fixing the cannula in the pulmonary artery or aorta.

2. A method according to claim 1, wherein said at least one cannula comprises a pair of cannulas having inflatable balloons are employed, one of said pair of cannulas being directed through the left ventricle into the aorta, the other of said pair of cannulas being directed into the right ventricle into the pulmonary artery, and inflating said balloons to fix the respective cannulas in said aorta and said pulmonary artery, whereby the transmural perforations of either the aorta or pulmonary artery and the left or right ventricle with cannulae are precluded to thereby eliminate damage to the aorta or pulmonary artery and ventricular muscle, and to diminish the propensity to embolization induced by transmural cannular introduction.

* * * * *